US010835501B2

(12) United States Patent
Smeeding et al.

(10) Patent No.: US 10,835,501 B2
(45) Date of Patent: Nov. 17, 2020

(54) PHARMACEUTICAL COMPOSITIONS COMPRISING A STATIN AND A CANNABINOID AND USES THEREOF

(71) Applicant: Indication BioScience LLC, Silverthorne, CO (US)

(72) Inventors: James Smeeding, Dallas, TX (US); Mathew Sherwood, Silverthorne, CO (US)

(73) Assignee: Indication BioScience LLC, Silverthorne, CO (US)

( * ) Notice: Subject to any disclaimer, the term of this patent is extended or adjusted under 35 U.S.C. 154(b) by 0 days.

(21) Appl. No.: 16/338,663

(22) PCT Filed: Oct. 1, 2017

(86) PCT No.: PCT/US2017/054685
§ 371 (c)(1),
(2) Date: Apr. 1, 2019

(87) PCT Pub. No.: WO2018/064654
PCT Pub. Date: Apr. 5, 2018

(65) Prior Publication Data
US 2019/0224141 A1  Jul. 25, 2019

Related U.S. Application Data

(60) Provisional application No. 62/403,067, filed on Oct. 1, 2016.

(51) Int. Cl.
| | | |
|---|---|---|
| *A61K 31/05* | (2006.01) | |
| *A61K 31/22* | (2006.01) | |
| *A61K 31/352* | (2006.01) | |
| *A61P 21/00* | (2006.01) | |
| *A61P 9/10* | (2006.01) | |
| *A61K 31/366* | (2006.01) | |
| *A61K 31/405* | (2006.01) | |
| *A61K 31/47* | (2006.01) | |
| *A61K 31/505* | (2006.01) | |
| *A61K 9/00* | (2006.01) | |
| *A61K 36/185* | (2006.01) | |

(52) U.S. Cl.
CPC .............. *A61K 31/05* (2013.01); *A61K 9/006* (2013.01); *A61K 31/22* (2013.01); *A61K 31/352* (2013.01); *A61K 31/366* (2013.01); *A61K 31/405* (2013.01); *A61K 31/47* (2013.01); *A61K 31/505* (2013.01); *A61K 36/185* (2013.01); *A61P 9/10* (2018.01); *A61P 21/00* (2018.01)

(58) Field of Classification Search
CPC ...... A61K 31/05; A61K 31/22; A61K 31/352; A61K 31/366; A61K 31/405; A61K 31/47; A61K 31/505; A61K 36/185; A61K 9/006; A61P 9/10; A61P 21/00
See application file for complete search history.

(56) References Cited

U.S. PATENT DOCUMENTS

| | | | |
|---|---|---|---|
| 4,681,893 | A | 7/1987 | Roth |
| 5,532,237 | A | 7/1996 | Gallant |
| 5,605,906 | A | 2/1997 | Lau |
| 6,251,852 | B1 | 6/2001 | Gould |
| 6,274,635 | B1 | 8/2001 | Travis |
| 6,410,588 | B1 | 6/2002 | Feldmann |
| 6,610,737 | B1 | 8/2003 | Garzon |
| 6,630,507 | B1 | 10/2003 | Hampson |
| 7,025,992 | B2 | 4/2006 | Whittle |
| 7,759,526 | B2 | 7/2010 | Mechoulam |
| 7,884,133 | B2 | 2/2011 | Mechoulam |
| 8,071,641 | B2 | 12/2011 | Weiss |
| 8,293,786 | B2 | 10/2012 | Stinchcomb |
| 9,017,737 | B2 | 4/2015 | Kikuchi |
| 9,205,063 | B2 | 12/2015 | Guy |
| 9,849,083 | B2 | 12/2017 | Sams |
| 9,974,767 | B2 | 5/2018 | Froehner |
| 10,098,867 | B2 | 10/2018 | Javid |
| 10,117,883 | B2 | 11/2018 | Kane |
| 10,155,018 | B1 | 12/2018 | Jenn |
| 10,166,202 | B2 | 1/2019 | Berry |
| 10,538,373 | B2 | 1/2020 | Whittle |
| 10,555,928 | B2 | 2/2020 | Blackmon |
| 2003/0162827 | A1 | 8/2003 | Venkataram |
| 2008/0033027 | A1* | 2/2008 | Bascomb .............. A61K 31/165 514/411 |
| 2008/0262079 | A1* | 10/2008 | Mach .................... A61K 31/535 514/454 |
| 2009/0022823 | A1 | 1/2009 | Ehrich |
| 2010/0158973 | A1 | 6/2010 | Weiss |
| 2012/0270845 | A1* | 10/2012 | Bannister ................. A61K 9/08 514/159 |
| 2013/0245110 | A1 | 9/2013 | Guy |

(Continued)

FOREIGN PATENT DOCUMENTS

| | | |
|---|---|---|
| WO | 2003007846 A1 | 1/2003 |
| WO | 2005034908 A2 | 4/2005 |

(Continued)

OTHER PUBLICATIONS

Jiang et al., Cannabidiol is a Potent Inhibitor of the Catalytic Activity of Cytochrome P450 2C19, Drug Metab. Pharmacokinet., vol. 28, No. 4, pp. 332-338 (2013).

(Continued)

*Primary Examiner* — Sarah Pihonak
(74) *Attorney, Agent, or Firm* — Calyx Law; Graham Pechenik

(57) ABSTRACT

The invention relates to pharmaceutical compositions comprising a statin and a cannabinoid, and their use for the treatment of hypercholesterolemia and atherosclerosis. It has been found that compositions combining a statin and a cannabinoid are improved over existing statin formulations. The compositions of the invention for example allow for a lower effective dose of statin and a reduction of the adverse effects seen with statins taken alone. Dosing ranges and formulations suitable for oral, buccal, and sublingual administration are disclosed. Various specific cannabinoids such as cannabidiol and synthetic cannabidiols selected for their anti-inflammatory, antioxidant, and anti-atherosclerotic effect are shown to be particularly advantageous.

15 Claims, No Drawings

(56) References Cited

U.S. PATENT DOCUMENTS

| | | | | |
|---|---|---|---|---|
| 2014/0348926 | A1* | 11/2014 | Hoffman | A61K 9/10 424/489 |
| 2016/0008320 | A1 | 1/2016 | Froehner | |

FOREIGN PATENT DOCUMENTS

| | | | | |
|---|---|---|---|---|
| WO | WO-2005102296 | A2 * | 11/2005 | A61K 45/06 |
| WO | 2008118141 | A2 | 10/2008 | |
| WO | 2009093018 | A1 | 7/2009 | |
| WO | 2012104654 | A1 | 8/2012 | |
| WO | 2016199148 | A1 | 12/2016 | |
| WO | 2019246632 | A1 | 12/2019 | |

OTHER PUBLICATIONS

Breuer et al., Fluorinated Cannabidiol Derivatives: Enhancement of Activity in Mice Models Predictive of Anxiolytic, Antidepressant and Antipsychotic Effects, PloS One, vol. 11, No. 7, e0158779 (2016).

Yamaori et al., Potent inhibition of human cytochrome P450 3A isoforms by cannabidiol: role of phenolic hydroxyl groups in the resorcinol moiety, Life Sci., vol. 88, pp. 730-736 (2011).

Huestis, Human Cannabinoid Pharmacokinetics, Chem. Biodivers., vol. 4, No. 8, pp. 1770-1804 (2007).

Haj et al., HU-444, a Novel, Potent Anti-Inflammatory, Nonpsychotropic Cannabinoid, J. Pharmacol. Exp. Ther., vol. 355, No. 1, pp. 66-75 (2015).

Rajesh et al., Cannabidiol attenuates cardiac dysfunction, oxidative stress, fibrosis, and inflammatory and cell death signaling pathways in diabetic cardiomyopathy, J. Am. Coll. Cardiol., vol. 56, No. 25, pp. 2115-2125 (2010).

Stone et al., 2013 ACC/AHA Guideline on the Treatment of Blood Cholesterol to Reduce Atherosclerotic Cardiovascular Risk in Adults, A Report of the American College of Cardiology/American Heart Association Task Force on Practice Guidelines, Circulation, vol. 129, Suppl. 2, pp. S1-S45 (2014).

Rosenson et al., Identification and Management of Statin-Associated Symptoms in Clinical Practice, Cardiovasc. Drugs Ther., vol. 31, No. 2, pp. 187-195 (2017).

Dormuth et al., Use of high potency statins and rates of admission for acute kidney injury, BMJ 346:f880 (2013).

Nagaraja et al., Synthesis of delta-3-cannabidiol and the derived rigid analogs, Univ. of Ariz., Dissertation to Dept. Pharm. Sci., Id. 8711643 (1987).

Cassol et al., Treatment with cannabidiol reverses oxidative stress parameters, cognitive impairment and mortality in rats submitted to sepsis by cecal ligation and puncture, Brain Res., vol. 1348, pp. 128-138 (2010).

Blair, Philip, "Comparing Cannabidiol to Statins for Heart Protection," Feb. 2015, available at: https://spacedoc.com/articles/cannabidiol-to-statins-heart-protection, retrieved May 18, 2020.

Graveline, Duane, "My Statin Story," May 2016, available at https://spacedoc.com/articles/my-statin-story, retrieved May 18, 2020.

Singla, et al., Cannabinoids and Atherosclerotic Coronary Heart Disease, Clin. Cardiol., vol. 35, No. 6, pp. 329-335 (2012).

Mach, et al., The Role of the Endocannabinoid System in Atherosclerosis, J. Neuroendocrin., vol. 20, Suppl. 1, pp. 53-57 (2008).

Schachter, Chemical, pharmacokinetic and pharmacodynamic properties of statins: an update, Fundamental & Clin. Pharmacol., vol. 19, pp. 117-125 (2004).

Rajesh, et al., Cannabidiol attenuates high glucose-induced endothelial cell inflammatory response and barrier disruption, Am. J. Physiol. Heart Circ. Physiol., vol. 293, pp. H610-H619 (2007).

Gudzune, et al., Effectiveness of Combination Therapy With Statin and Another Lipid-Modifying Agent Compared With Intensified Statin Monotherapy, Annals of Inter. Med., vol. 160, No. 7, pp. 468-477 (2014).

Roth, Marijuana and your heart, Nature, vol. 434, pp. 708-709 (2005).

Steffens, et al., Low dose oral cannabinoid therapy reduces progression of atherosclerosis in mice, Nature, vol. 434, pp. 782-086 (2005).

Sultan et al., A systematic Review and Meta-Analysis of the Haemodynamic Effects of Cannabidiol, Front. Pharmacol., vol. 8, Article 81 (2017).

Jadoon, et al., A single dose of cannabidiol reduces blood pressure in healthy volunteers in a randomized crossover study, JCI Insight, vol. 2(12):e93760 (2017).

Zuardi, et al., Cannabidiol: from an inactive cannabinoid to a drug with wide spectrum of action, Braz. J. Psychiatry, vol. 30, No. 3, pp. 271-280 (2008).

Mead, et al., The Untold Story of the Cannabidiol (CBD) Revolution, US Neurology, vol. 14, Suppl. 3, pp. 2-8 (2018).

PACHER, et al., The endocannabinoid system as an emerging target of pharmacotherapy., Pharmacol Rev., vol. 58, pp. 389-462 (2006).

* cited by examiner

PHARMACEUTICAL COMPOSITIONS COMPRISING A STATIN AND A CANNABINOID AND USES THEREOF

CROSS REFERENCE

This application is a U.S. national phase application under 35 U.S.C. § 371 of co-pending International Application No. PCT/US17/54685, filed on Oct. 1, 2017, which claims the benefit of U.S. Provisional Application No. 62/403,067, filed Oct. 1, 2016, which are incorporated herein by reference in their entirety.

FIELD OF THE INVENTION

The present invention generally relates to pharmaceutical compositions comprising a statin and a cannabinoid which may be used in the treatment of subjects with elevated cholesterol levels.

BACKGROUND OF THE INVENTION

Cholesterol is a waxy, fat-like substance that is naturally found in the bloodstream and in all cells of the human body, and is needed for the body to function normally. However, the presence of abnormally high levels of cholesterol in the blood, known as hypercholesterolemia, is a major risk factor for heart disease and stroke. Indeed, people with high cholesterol have approximately twice the risk of acquiring heart disease, the leading cause of death for both men and women in the United States.

Cholesterol travels through the bloodstream in small packages called lipoproteins, which take two forms: low-density lipoproteins (LDL) and high-density lipoproteins (HDL). High levels of LDL cholesterol in particular (referred to as "bad cholesterol") increases the risk of heart disease and stroke by causing arterial plaque buildup ("atherosclerosis"). By contrast, HDL cholesterol (or "good cholesterol") absorbs and carries cholesterol to the liver, which aids in flushing it from the body. According to statistics from the Centers for Disease Control and Prevention (CDC), over one-third of American adults have elevated levels of LDL cholesterol.

Although the atherosclerotic progression is not fully understood, it is believed to be caused by inflammatory processes resulting in part from retained LDL cholesterol, which becomes prone to oxidation when inside arterial walls. The oxidation of LDL attracts white blood cells (WBCs), which penetrate into the arterial walls and transform into macrophages. The macrophages scavenge for and absorb the oxidized LDL, and form "foam cells," which attempt to recruit HDL particles to process the LDL particles and remove the fats. But if the level of LDL particles is too high relative to the level of HDL particles, foam cells cannot process all of the oxidized LDL, and will eventually die and burst, leaving behind cholesterol and other debris in the artery wall. This attracts additional WBCs, creating a feedback loop that results in further inflammation, and eventually an accumulation of material (a "plaque"). If a plaque ruptures, it can lead to the occlusion of blood vessels, cutting off blood supply, and potentially causing a heart attack or stroke. Reducing LDL cholesterol is therefore viewed as a key to preventing or slowing the progression of atherosclerosis, and lowering the likelihood of related cardiovascular incidents.

Besides lifestyle changes, such as a modified diet and increased physical exercise, the primary form of treatment for high LDL cholesterol is the administration of drugs from the class known as HMG-CoA reductase inhibitors, commonly referred to as "statins."

Statins

Statins work by inhibiting the HMG-CoA reductase enzyme, which plays a central role in the production of cholesterol in the liver and produces about 70% of total cholesterol in the body. By decreasing the liver's production of cholesterol, statins lower total blood cholesterol and LDL cholesterol. Statins also increase the liver's ability to remove LDL cholesterol from the blood.

Various statins have been developed and brought to market, including atorvastatin (Lipitor®, Pfizer), fluvastatin (Lescol®, Novartis), lovastatin (Mevacor®, Merck; Altoprev®, Andrex), pitavastatin (Livalo®, Kowa Pharms.), pravastatin (Pravachol®, Bristol-Myers Squibb), rosuvastatin (Crestor®, Astra Zeneca), and simvastatin (Zocor®, Merck).

Statins lower LDL cholesterol levels more than any other current drug therapy, and are the most effective medications presently used for managing elevated LDL cholesterol. Nonetheless, the use of statins to treat hypercholesterolemia suffers from significant drawbacks. In observational studies, 10-15% of people who take statins experience muscle problems, including such adverse effects as muscle discomfort and weakness, myositis (i.e., muscle inflammation) and rhabdomyolysis (i.e., muscle breakdown). The incidence of such myopathic (i.e., muscle-related) reactions increases with older age, use of interacting medications such as fibrates, and hypothyroidism. Despite numerous publications describing statin-induced myopathy, however, the mechanism has not been elucidated.

Statin use also is correlated with an elevated risk of developing kidney problems. Statin use is associated with a 50% increase in risk of acute renal failure, with evidence of raised risk within the first year of use, and greater risk at increased dosages. The occurrence of kidney injury could be related to the increased risk of muscle damage when taking statins. Breakdown products of damaged muscle cells are released into the bloodstream, and some of these, such as the protein myoglobin, are harmful to the kidneys and may lead to kidney failure. Additionally, statins have been shown to block the production of coenzyme Q10 (a substance in the body that helps break down food), which also may lead to kidney injury. Other serious adverse effects of statin use include liver injury, increased risk of diabetes mellitus, cognitive impairment, neuropathy, pancreatic dysfunction, and sexual dysfunction.

All commonly used statins have been shown to cause similar adverse effects, although rates of those adverse effects can differ across the class. Some researchers have suggested that hydrophilic statins (such as fluvastatin, rosuvastatin, and pravastatin) are less toxic than lipophilic statins (such as atorvastatin, lovastatin, and simvastatin), but other studies have not found a connection. The risk of myopathy has been suggested to be lowest with pravastatin and fluvastatin, possibly because they are more hydrophilic and as a result have less muscle penetration. Users of certain "high potency" statins (i.e., ≥10 mg per day rosuvastatin, ≥20 mg per day atorvastatin, and ≥40 mg per day simvastatin) were shown to be 34% more likely to be hospitalized with acute kidney injury within 120 days after starting treatment compared to "low potency" statins. (Dormuth et al., Use of high potency statins and rates of admission for acute kidney injury, BMJ 2013.) One statin, cerivastatin (Baycol®/Lipobay®, Bayer) was withdrawn from the market in 2001 following 52 deaths attributed to kidney failure from drug-related rhabdomyolysis, a rate that was ten times more common than with other approved statins, and greatest in patients on the highest (0.8 mg/day) dose of cerivastatin, and in patients who took gemfibrozil and other fibrates concomitantly.

Different approaches have been attempted to reduce the adverse effects of statins. For example, some newer statins, characterized by longer pharmacological half-lives and more cellular specificity, have been shown to have a better ratio of efficacy to adverse effect rates. Nevertheless, the occurrence of serious adverse effects has not yet been eliminated nor reduced satisfactorily. Indeed, for some patients experiencing statin-associated adverse effects, physicians may simply decrease the dose or discontinue statin therapy altogether. However, this limits effective treatment and puts patients at increased risk of cardiovascular morbidity and mortality. (Rosenson et al., Identification and Management of Statin-Associated Symptoms in Clinical Practice, Cardiovasc. Drugs Ther., 31:187-95 (2017) at 188, 194, and references cited.)

Therefore, a need continues to exist for therapeutically effective pharmaceutical compositions for the treatment of hypercholesterolemia that do not have the drawbacks of current treatment regimens with statins, A significant advancement in the art would occur with the development of such pharmaceutical compositions. The subject of the present invention is a novel approach involving pharmaceutical compositions that combine a statin with a cannabinoid, such as the cannabinoid known as cannabidiol (CBD).

Cannabinoids

Cannabinoids are a diverse class of small molecules that are grouped together because of their ability to act on cannabinoid receptors found in the brain and throughout the central and peripheral nervous systems of humans and other mammals. Cannabinoid receptors are a class of cell membrane receptors under the G protein-coupled receptor superfamily. There are two primary known types of cannabinoid receptors, known as cannabinoid 1 ($CB_1$) and cannabinoid 2 ($CB_2$). $CB_1$ receptors are found primarily in the central nervous system (i.e., the brain and spinal cord), as well as in the lungs, liver and kidneys. $CB_2$ receptors are found primarily in the immune system and in hematopoietic cells. Cannabinoids also activate another G protein-coupled receptor known as GPR55, and are thought to activate GPR119 and GPR18.

Cannabinoids produced endogenously in humans and other mammals are termed endocannabinoids. Taken together, these endocannabinoids and the endogenous cannabinoid receptors they act on (along with the enzymes for their synthesis and degradation) form the endocannabinoid system. The endocannabinoid system has been shown or suggested to be involved in a variety of physiological processes including appetite, digestion, pain-sensation, mood, memory, reproduction, stress response, immune function, thermoregulation, energy balance, and sleep.

Cannabinoids also have been isolated from plants, including at least 85 from the *Cannabis* plant, among other plants including echinacea, kava, tea, and flax. Cannabinoids from plants are termed phytocannabinoids. These non-endogenous cannabinoids also act on cannabinoid receptors in the body, and they have many structural similarities with endogenous cannabinoids, and likewise have the ability to easily cross the blood-brain barrier, and show weak toxicity and few side effects. Among the naturally-occurring phytocannabinoids from *cannabis*, tetrahydrocannabinol (THC), cannabidiol (CBD), and cannabinol (CBN) are the three major constituents.

Tetrahydrocannabinol (THC) is one of the most widely-known cannabinoids derived from the *Cannabis* plant, particularly because of its psychoactive effects. The psychoactive effects of THC are thought to be primarily because of its interaction with $CB_1$ receptors. Besides the principle THC isomer (−)-trans-$\Delta^9$-tetrahydrocannabinol ($\Delta^9$-THC), numerous other double bond and stereo isomers of THC have been derived from *Cannabis*.

Cannabidiol (CBD), unlike THC, does not produce psychoactive effects in humans (and in fact, can antagonize those effects). CBD is reported to demonstrate numerous pharmacological properties. For instance, CBD has been shown to exert analgesic, antioxidant, anti-inflammatory, antiemetic, anticonvulsant, antipsychotic, anxiolytic, antidepressant, anticompulsive, antitumoral, neuroprotective, and immunomodulatory effects. CBD acts as an indirect antagonist of $CB_1$ and $CB_2$ cannabinoid receptor agonists, and is also an inverse agonist of $CB_2$ receptors. CBD also acts as an antagonist to other ligands at $CB_1$ and $CB_2$ receptors. Interaction with $CB_2$ receptors appears to be primarily responsible for the anti-inflammatory and other therapeutic effects of *cannabis* seen in animal models.

Numerous mechanisms of action supporting the pharmacological effects of CBD have been demonstrated or suggested. For example, mechanisms that have been shown or suggested to be related to the actions of CBD include activation of TRPV1 channels, inhibition of uptake and metabolism of the endocannabinoid anandamide, inhibition of adenosine uptake, antagonism of GPR55, agonism of PPARγ and 5-$HT_{1A}$ receptors, and increase of intracellular calcium ions. CBD also has been shown or suggested to be related to reductions in mitochondrial superoxide generation, NF-κB activation, levels of tumor necrosis factor (TNF) alpha and inducible nitric oxide synthase (iNOS), adhesion molecule expression, monocyte-endothelial adhesion, trans-endothelial migration of monocytes, disruption of endothelial barrier function in human coronary arteries, and reduction in cardiac cell death. Lymphoid cells that are important activators of macrophages and T-cells secrete less interferon-gamma and proliferate more slowly. Macrophage infiltration, a crucial step for the development of atherosclerosis, is inhibited in vitro. CBD protects cells against oxidative stress by decreasing the production of reactive oxygen species (ROS) and, in particular central neurons, from apoptosis (programmed cell death).

The third major naturally-occurring phytocannabinoid in *Cannabis* plants, cannabinol (CBN), is weakly psychoactive, and found only in trace amounts. CBN has been shown to have analgesic properties but otherwise is thought to exert minimal pharmacological effects in the central nervous system. CBN has an affinity to $CB_2$ receptors, and also acts as a partial agonist of $CB_1$ receptors (but with lower affinity than THC).

Other naturally-occurring phytocannabinoids in *Cannabis* plants include, among numerous more, cannabigerol (CBG), cannabinodiol (also known as cannabidinodiol) (CBDL, CBND), cannabichromene (CBC), cannabielsoin (CBE), cannabicyclol (CBL), cannabicitran (CBT), cannabivarin (CBV), cannabidivarin (CBDV), tetrahydrocannabivarin (THCV), cannabichromevarin (CBCV), cannabigerovarin (CBGV), and cannabigerol monomethyl ether (CBGM).

Synthetic cannabinoids are compounds which have been made in a laboratory by means of chemical synthesis.

Synthetic cannabinoids may have the same structure as endocannabinoids or phytocannabinoids, or may have modifications, including those resulting in or designed to cause alterations in the way the cannabinoids function and behave. Numerous synthetic variants and analogues of cannabinoids have been created, and some have been shown to have altered or enhanced activity. For example, Breuer et al. (Fluorinated Cannabidiol Derivatives: Enhancement of Activity in Mice Models, PLOS ONE, 2016) report the synthesis of three fluorinated CBD derivatives, one of which showed considerably greater potency than CBD in behavioral assays in mice predictive of anxiolytic, antidepressant, antipsychotic, and anticompulsive activity.

Cannabinoids also may be obtained from bioengineered organisms, such as bacteria or yeast. For example, yeast can be bioengineered to produce cannabinoids by inserting genes that produce the appropriate enzymes and/or by altering the natural metabolic pathway to achieve the production of a desired compound from sugars, the main carbon source available to yeast. These compounds can then be obtained and purified. Through such means, cannabinoids may be obtained that are the same as those extracted from *Cannabis* plants, or that are modifications thereof.

Drug Bioavailability and Metabolism

Bioavailability of a drug refers to the fraction of an administered dose of the drug that reaches the systemic circulation; that is, the proportion of the total dose that enters the bloodstream and is able to produce an effect (typically calculated as the AUC, or "area under the curve," on a plot of the concentration of the drug in the blood over time). By definition, when a drug is administered intravenously, its bioavailability is 100%, because it is administered directly into the bloodstream. By comparison, when drugs are administered via other routes (such as orally), their bioavailability generally decreases. This is due to incomplete absorption and first-pass metabolism (i.e., metabolism that occurs before a drug reaches systemic circulation).

The metabolism of drugs inside living organisms involves a series of chemical reactions organized into metabolic pathways, in which the drug is broken down through a series of steps into other chemicals, by a sequence of specialized enzymes. The enzymes act as catalysts that regulate the reactions and allow them to proceed more rapidly. The rate of metabolism in part determines the duration and intensity of a drug's pharmacologic action, because of its effect on drug bioavailability.

Cytochrome P450 proteins (abbreviated as CYPs) are a superfamily of over 21,000 distinct enzymes found in virtually all organisms. CYPs in humans are found in the intestines and liver, and catalyze many reactions involved in drug metabolism (and also play a role in the synthesis of steroids, cholesterol, and other lipids). The human CYP3A subfamily is involved in the metabolism of more than 50% of drugs clinically used, with CYP3A4 in particular being the most abundant isoform expressed in adult human livers.

CYP enzymes are responsible for the presystemic metabolism of certain statins in the intestines and liver. Lovastatin, simvastatin, and atorvastatin are all substrates for CYP3A4 (as well as the withdrawn statin cerivastatin, and mevastatin, which was never marketed). Lovastatin and simvastatin undergo extensive (90% or more) metabolism by CYP3A4, resulting in very low bioavailability. Atorvastatin does not undergo as extensive presystemic metabolism, and hence its bioavailability is relatively higher.

Other statins are metabolized by different CYP enzymes, such as rosuvastatin (CYP2C9 and CYP2C19), pitavastatin (CYP2C9), and fluvastatin (primarily CYP2C9, and to a lesser degree CYP2C8 and CYP3A4), or by a different enzymatic system entirely (pravastatin, metabolized by sulfation). Although these different CYP enzymes are not as involved in drug metabolism as CYP3A4, they still play an important role for many drugs (with CYP2C19, for instance, acting on over 10% of drugs in clinical use).

It is commonly understood that the risk of certain adverse events may increase when a statin is taken together with another compound that is also a substrate for or inhibitor of the same CYP enzymes. By competitively binding to the same CYP enzymes as the statin, or otherwise inhibiting the ability of those CYP enzymes to bind with the statin, the other compound decreases the rate of metabolism of the statin, and consequently increases its bioavailability. For example, potent CYP3A4 inhibitors such as itraconazole (an antifungal medication) can produce two- to four-fold increases in atorvastatin serum concentrations, and 10- to 20-fold increases in lovastatin and simvastatin serum concentrations.

Increases in the bioavailability of the statin can result in increased risk of adverse events. For instance, the risk of statin-associated myopathy with lovastatin, simvastatin, and to a lesser extent atorvastatin, is increased by concomitant therapy with the macrolide antibiotics erythromycin and clarithromycin because of their CYP3A4 metabolism and resultant increase in statin bioavailability. Increased bioavailability along with myositis and rhabdomyolysis also have been reported following concurrent use of simvastatin or lovastatin with cyclosporine A, mibefradil, and nefazodone. The calcium-channel blocker verapamil, another CYP3A4 inhibitor, is also known to increase the risk of statin-associated myopathy. And as noted above, the CYP3A4-metabolised statin cerivastatin was withdrawn from the market because of the increased risk of kidney failure from drug-related rhabdomyolysis, a risk that was highest in patients who took it together with fibrates (such as gemfibrozil) which are also substrates for CYP3A4. Similar interactions occur with statins that are metabolized by other CYP enzymes and the compounds that compete for or inhibit the activity of those enzymes.

The metabolism of CBD administered orally is comprised of four primary systems: the enzymes of the gastrointestinal lumen, gut wall enzymes, bacterial enzymes, and hepatic enzymes. The hepatic metabolism for CBD occurs at CYP3A4, and to a lesser extent, CYP2C19. As a result of this metabolic activity, the bioavailability of CBD administered orally in humans is relatively poor, being approximately 6%. In addition to being metabolized by CYP3A4 and CYP2C19 enzymes in the liver, CBD also functions as a potent inhibitor of those enzymes (see Yamaori et al., Potent inhibition of human cytochrome P450 3A isoforms by cannabidiol, Life Sci., 88:730-36 (2011); Jiang et al., Cannabidiol is a potent inhibitor of the catalytic activity of cytochrome P450 2C19, Drug Metab. Pharmacokinet., 28(4):332-38 (2013)). CBD is also a potent inhibitor of various other CYP enzymes, including CYP2C9 (see Jiang at 333 and references cited).

Just as compounds which affect CYP3A availability will affect the bioavailability of CYP3A-metabolized statins, by the same token, compounds which affect CYP3A availability will affect CBD bioavailability. For example, the antifungal medication ketoconazole, a strong inhibitor of CYP3A4, has been demonstrated to increase the plasma concentration of CBD by about two-fold; while the antibiotic rifampin, a CYP3A4 inducer, reduced CBD levels by 50-60%. Other CYP3A4 inhibitors and inducers would be expected to have a similar effect on CBD plasma concentrations if coadministered. The same would be true with inhibitors and inducers of other CYP enzymes, such as CYP2C19 and CYP2C9.

Despite such generalized knowledge and use of statins and cannabinoids, the teachings demonstrating the use of statins for treatment of high cholesterol, along with the teachings demonstrating the properties of cannabinoids such as CBD, could not have predicted the benefits that could be achieved by administration of a statin and a cannabinoid in combination, as in the pharmaceutical compositions of the present invention. Indeed, knowledge that the risk of adverse events may increase when a statin is taken together with another compound that is also a substrate for or inhibitor of the same CYP enzymes would have effectively taught away from the combination of a cannabinoid and a statin; whereas the present invention discloses unexpectedly that such a combination in fact can reduce the number and severity of adverse events.

INCORPORATION BY REFERENCE

Each patent, publication, and non-patent literature cited in the application is hereby incorporated by reference in its entirety as if each was incorporated by reference individually.

SUMMARY OF THE INVENTION

It is an object of the present invention to provide pharmaceutical compositions comprising a pharmaceutically effective amount of a statin, in combination with such other compounds so as to convey or enhance the antihypercholesterolemic effect of the statin while preferably also reducing or eliminating the drawbacks of current treatment regimens with statins.

It is an object of the present invention to provide such pharmaceutical compositions where the statin is combination with a cannabinoid.

In preferred embodiments, it is an object of the present invention to provide pharmaceutical compositions where the statin is in combination with a cannabidiol.

In more preferred embodiments, it is an object of the present invention to provide pharmaceutical compositions where the statin is in combination with $\Delta^2$-cannabidiol.

It is another object of the invention to provide pharmaceutical compositions of a statin and a cannabinoid that exhibit enhanced bioavailability of the statin.

In preferred embodiments, the bioavailability of both the statin and the cannabinoid are enhanced.

In other preferred embodiments, both the and the cannabinoid are substrates of the same CYP enzyme.

In more preferred embodiments, both the statin and the cannabinoid are substrates of CYP3A4.

In other more preferred embodiments, both the statin and the cannabinoid are substrates of CYP2C19 and/or CYP2C9.

In more preferred embodiments, the cannabinoid is a synthetic cannabidiol.

In still more preferred embodiments, the cannabinoid is a synthetic cannabidiol that shows enhanced inhibitory activity of the CYP3A4 enzyme compared to naturally-occurring cannabidiols.

In other more preferred embodiments, the cannabinoid is a synthetic cannabidiol that shows enhanced inhibitory activity of the CYP2C19 and/or CYP2C9 enzyme compared to naturally-occurring cannabidiols.

In other more preferred embodiments, the cannabinoid is a synthetic cannabidiol that exhibits enhanced anti-inflammatory activity.

In other more preferred embodiments, the cannabinoid is a synthetic cannabidiol that exhibits enhanced antioxidant activity.

In other more preferred embodiments, the cannabinoid is a synthetic cannabidiol that exhibits enhanced anti-atherosclerotic activity.

In the most preferred embodiments, the cannabinoid is a synthetic cannabidiol that exhibits multidimensional enhanced activity, being selected for possessing two or more of: enhanced CYP enzyme inhibitory activity; enhanced anti-inflammatory activity; enhanced antioxidant activity; and enhanced anti-atherosclerotic activity.

In other preferred embodiments, the cannabinoid is obtained by means of a bioengineered organism such as bacteria or yeast.

It is another object of the invention to provide commercially practicable pharmaceutical compositions of a statin and a cannabinoid that are readily formulated and administered.

It is yet another object of the invention to provide pharmaceutical compositions of a statin and a cannabinoid that exhibit enhanced bioavailability of the statin, but where such increased bioavailability is without concomitant increases in the risk of myopathy or other serious adverse effects.

It is another object of the present invention to provide dose ranges at which the pharmaceutical compositions of a statin and a cannabinoid (i.e., the "statin-cannabinoid compositions") shall be therapeutically effective.

It is an additional object of this invention to provide statin-cannabinoid compositions which comprise a cannabinoid in an amount effective to lower the effective dose of the selected statin.

It is another object of the present invention to provide statin-cannabinoid compositions in which the amount of cannabinoid is effective to reduce the highest dosage of the statin by a measurable amount, such as 25%, 50%, or 75%, when compared to the highest recommended dosage when the statin is administered alone, without any noticeable loss of therapeutic effect.

It is another object of the present invention to provide a method of treating a human with a statin-cannabinoid composition, in which the amount of cannabinoid is effective to reduce the dosage of the statin by a measurable amount, such as 25%, 50%, or 75%, relative to the previous prescribed dosage of the statin when administered alone, without any noticeable loss of therapeutic effect.

It is an additional object of this invention to provide statin-cannabinoid compositions that safely allow for higher dosages of the selected statin without the risk (or with a substantially reduced risk) of severe statin-induced adverse effects (e.g., myolysis or rhabdomyolysis).

In certain preferred embodiments, it is an additional object of the invention to provide pharmaceutical compositions which are without psychoactive effect.

It is an additional object of this invention to provide a method of treating hypercholesterolemia in a subject, the method comprising administering to the subject a pharmaceutical composition of the invention.

It is another object of the invention to provide a method of inhibiting cholesterol biosynthesis in a patient in need of such treatment by administering an effective amount of a pharmaceutical composition as defined herein.

It is an additional object of this invention to provide a method of treating or preventing rhabdomyolysis or statin-associated myopathy in a subject, the method comprising administering to the subject a pharmaceutical composition of the invention.

These and other objects, features, and advantages of the present invention may be more clearly understood and appreciated from a review of the following detailed description of the disclosed embodiments and by reference to the appended claims. The foregoing summary has been made with the understanding that it is to be considered as a brief and general synopsis of only some of the objects and embodiments, is provided solely for the benefit and convenience of the reader, and is not intended to limit in any manner the scope, or range of equivalents, to which the appended claims are lawfully entitled.

Definitions

The following definitions are provided to better elucidate the present invention and to guide those of ordinary skill in the art in the practice of the present invention. Unless otherwise noted, terms are to be understood according to conventional usage by those of ordinary skill in the relevant art.

"Botanical drug substance" is as defined in the Guidance for Industry Botanical Drug Products, June 2004, US Department of Health and Human Services, Food and Drug Administration Center for Drug Evaluation and Research ("2004 FDA Botanical Drug Guidance"), i.e., "A drug substance derived from one or more plants, algae, or macroscopic fungi. It is prepared from botanical raw materials by one or more of the following processes: pulverization, decoction, expression, aqueous extraction, ethanolic extraction, or other similar process. It may be available in a variety of physical forms, such as powder, paste, concentrated liquid, juice, gum, syrup, or oil. A botanical drug substance can be made from one or more botanical raw materials. A botanical drug substance does not include a highly purified or chemically modified substance derived from natural sources."

"Botanical drug product" is as defined in the 2004 FDA Botanical Drug Guidance, i.e., "A botanical product that is intended for use as a drug; a drug product that is prepared from a botanical drug substance."

"Cannabinoid" refers to all naturally-occurring, synthetic, or bioengineered compounds that can mimic the behavior of endogenous or plant-derived cannabinoids (e.g., acting on $CB_1$, $CB_2$, and GPR55 receptors), or that have structures that are modifications of endogenous or plant-derived cannabinoids, or are otherwise enantiomers, precursors, prodrugs, metabolites, derivatives, analogs, or variants thereof. Many such compounds have been described (see, e.g., U.S. Pat. Nos. 5,532,237; 5,605,906; 5,631,297; 6,410,588; 6,610,737; 6,630,507 at cols. 3:36-6:66; 6,274,635 at cols. 8:63-20:11; and 8,071,641 at cols. 5:38-6:26; and references cited), and numerous other cannabinoids would be recognized or known to those of ordinary skill in the art, or be able to be created by the practice of ordinary skill in the art.

"Cannabidiol" or "CBD" refers to $\Delta^2$-cannabidiol (i.e., 2-[(1R,6R)-6-isopropenyl-3-methylcyclohex-2-en-1-yl]-5-pentylbenzene-1,3-diol), its seven double bond isomers and their 30 stereoisomers (see Nagaraja, Synthesis of delta-3-cannabidiol and the derived rigid analogs, Ariz. Univ. 1987), and such other naturally-occurring, synthetic, or bioengineered enantiomers, metabolites, derivatives, analogs, or variants thereof as would be recognized or known to those of ordinary skill in the art, or be able to be created by the practice of ordinary skill in the art. Exemplary cannabidiols include those described in U.S. Pat. No. 6,274,635 at cols. 17:41-20:11; U.S. Pat. No. 7,759,526 at cols. 1:65-2:35; and U.S. Pat. No. 8,071,641 at cols. 6:36-7:25; and references cited. Within the scope of cannabidiols are also its precursors and prodrugs, for example those described in U.S. Pat. No. 8,293,786, and the enantiomers, metabolites, derivatives, analogs, and variants thereof.

"*Cannabis*-derived drug substance" means botanical drug substances which are derived from *Cannabis* plants (including plant parts, plant part biomass, and plant exudates), for example primary extracts prepared by processes including maceration, percolation, extraction with solvents such as C1 to C5 alcohols (e.g., ethanol), Norflurane (HFA134a), HFA227, liquid carbon dioxide under pressure and extraction using a hot gas.

"*Cannabis*-derived drug product" means a primary *cannabis* extract that is further purified, for example by supercritical or subcritical extraction, vaporization and chromatography. It will be known to those of skill in the art that when solvents such as those listed above (see "*Cannabis*-derived drug substance") are used to prepare primary extracts, the resultant extract may contain non-specific lipid-soluble material. Those of skill in the art will know that such impurities can be removed by a variety of processes including winterization (e.g., by chilling to −20° C. followed by filtration to remove waxy ballast), extraction with liquid carbon dioxide, and distillation.

"*Cannabis* plant" is defined to encompass all wild-type *Cannabis saliva*, *Cannabis indica*, and *Cannabis ruderalis* plants, as well as genetic crosses, self-crosses, hybrids, variants, and chemovars thereof.

"Optional" or "optionally" means that the subsequently described event or circumstance may but need not occur, and that the description includes instances where the event or circumstance occurs and instances in which it does not.

"Pharmaceutically acceptable" as used in connection with an excipient, carrier, or diluent means an excipient, carrier, or diluent that is useful in preparing a pharmaceutical composition that is generally safe, non-toxic and neither biologically nor otherwise undesirable for veterinary use and/or human pharmaceutical use.

"Psychoactive effect" means objectively or subjectively apparent alterations in behavior, perception, mood, or consciousness.

"Statin" means a drug from the class known as HMG-CoA reductase inhibitors. Statins within the scope of this invention therefore include those drugs which have already been developed and approved, for example atorvastatin (Lipitor®, Pfizer), fluvastatin (Lescol®, Novartis), lovastatin (Mevacor®, Merck; Altoprev®, Andrex), pitavastatin (Livalo®, Kowa Pharmaceuticals), pravastatin (Pravachol®, Bristol-Myers Squibb), rosuvastatin (Crestor®, Astra Zeneca), and simvastatin (Zocor®, Merck). Statins would be understood to include all dosage forms and formulations of the above (e.g., immediate as well as extended release). Statins also should be understood to include any other HMG-CoA reductase inhibitors, whether already known and characterized (such as mevastatin, velostatin, dihydrocompactin, dalvastatin, cerivastatin, carvastatin, crilvastatin, bevastatin, cefvastatin, and glenvastatin), currently in the development or approval process, or as yet to be developed, that function by inhibiting the HMG-CoA reductase enzyme, or otherwise function in a way that is equivalent or understood to be equivalent by one of skill in the art. Statins shall also be understood to include all pharmaceutically-acceptable amorphous and crystalline forms and salts, esters, and lactone forms, for example as described for atorvastatin in U.S. Pat. App. No. 2003/0162827A1, and references cited.

"CYP3A4-metabolized statins" means those statins whose route of metabolization in the liver includes the Cytochrome P450 isoenzyme CYP3A4. Examples of CYP3A4-metabolized statins include lovastatin, simvastatin, and atorvastatin.

"CYP2C19-metabolized statins" means those statins whose route of metabolization in the liver includes the Cytochrome P450 isoenzyme CYP2C19. An example of a CY2C19-metabolized statin is rosuvastatin.

"CYP2C9-metabolized statins" means those statins whose route of metabolization in the liver includes the Cytochrome P450 isoenzyme CYP2C9. Examples of CYP3A4-metabolized statins include rosuvastatin, fluvastatin, and pitavastatin.

"Therapeutically effective amount" means the amount of a pharmaceutical composition that, when administered to a patient for treating a condition, disorder, or disease, is sufficient to effect such treatment for the condition, disorder, or disease. The amount constituting a "therapeutically effective amount" of the present invention will vary depending on the statin and the cannabinoid used, the severity of the condition, disorder, or disease, and the age, weight, and other medically-relevant characteristics of the subject to be treated, and such a determination (if not already made) will be able to be rendered without undue experimentation by one of skill in the art.

"Therapeutic effect" means the responses(s) in a patient after treatment which are judged to be desirable and beneficial. For treatment of patients having symptoms of hypercholesterolemia, such responses shall include, for example, reductions in total blood cholesterol, reductions in LDL cholesterol, reductions in triglyceride levels, regression of arterial atherosclerotic plaque, reduced risk of cardiovascular and cerebrovascular events, and other such measurements, benefits, and surrogate or clinical endpoints, whether alone or in combination, as would be understood to those of ordinary skill. Accordingly, "without loss of therapeutic effect" means that the observed response(s) in the patient are not significantly diminished following a change in treatment regimen, as would be understood to one of ordinary skill.

"Treating" "treatment" of a disease includes (i) inhibiting the disease, i.e., arresting or reducing the development of the disease or its clinical symptoms; or (ii) relieving the disease, i.e., causing regression of the disease or its clinical symptoms. Inhibiting the disease, for example, would include prophylaxis. Hence, one of skill in the art will understand that a therapeutic amount necessary to effect treatment for purposes of this invention will, for example, be an amount that provides for objective indicia of improvement in patients having symptoms of hypercholesterolemia. Such indicia of improvement shall include, for example, reductions in total blood cholesterol, reductions in LDL cholesterol, reductions in triglyceride levels, regression of arterial atherosclerotic plaque, reduced risk of cardiovascular and cerebrovascular events, and other such measurements, benefits, and surrogate or clinical endpoints, whether alone or in combination, as would be understood to those of ordinary skill.

When introducing elements of the present invention or the preferred embodiments thereof, the articles "a," "an," "the," and "said" are intended to mean that there are one or more of the elements. The terms "comprising," "including," and "having" are intended to be inclusive and not exclusive (i.e., there may be other elements in addition to the recited elements).

DETAILED DESCRIPTION OF THE INVENTION

Among the various aspects of the present invention are pharmaceutical compositions comprising a statin, a cannabinoid, and a pharmaceutically-acceptable carrier, diluent, or excipient. While the present invention is described in terms of particular embodiments and applications, it is not intended that these descriptions in any way limit its scope to any such embodiments and applications, and it will be understood that many modifications, substitutions, changes, and variations in the described embodiments, applications, and details of the invention illustrated herein can be made by those skilled in the art without departing from the spirit of the invention, or the scope of the invention as described in the appended claims.

Central to the present invention is the discovery that a statin taken in combination with a cannabinoid, such as a cannabidiol, will exhibit a synergistic effect. The present invention thus advantageously offers pharmaceutical compositions that are substantially improved over existing statin formulations. For example, the statin-cannabinoid compositions of the present invention enable a lower dose of statin without loss of therapeutic effect, and can reduce the number and severity of adverse effects compared to statins used alone. Further, the specific formulations of the invention provide for improved bioavailability of the statin and cannabinoid used. Other features and advantages will emerge from the following description of the invention.

Statin+Cannabinoid Combinations

The statins used in the pharmaceutical compositions of the present invention are preferably those that are commercially available and approved for use in treating hypercholesterolemia. These include atorvastatin, fluvastatin, lovastatin, pitavastatin, pravastatin, rosuvastatin, and simvastatin.

Preferably, the statins used are CYP2C19-metabolized statins or CYP2C9-metabolized statins.

More preferably, the statins used are CYP3A4-metabolized statins.

More preferably still, the statins used are CYP3A4-metabolized statins from the group consisting of atorvastatin, lovastatin, and simvastatin.

The cannabinoids used in the pharmaceutical compositions of the invention are preferably one or more cannabidiols.

More preferably, the cannabinoids used shall be $\Delta^2$-cannabidiol, and more preferably still, $\Delta^2$-cannabidiol that is synthetic or obtained through bioengineered means.

More preferably still, the cannabinoids used shall be from the group consisting of synthetic cannabidiols selected for their CYP enzyme affinity (e.g., their CYP3A4, CYP2C19, and/or CYP2C9 enzyme affinity), their anti-inflammatory, antioxidant, or anti-atherosclerotic effects, or a combination of such traits.

The cannabinoids used in the compositions of the invention may be obtained as natural compounds (e.g., as a *Cannabis*-derived drug substance or drug product), as synthetic compounds, from a bioengineered organism (e.g., bacteria or yeast), or as a combination thereof.

Thus, in one embodiment of the invention, the compositions shall be derived from *Cannabis* plants, by extraction or other means, and shall comprise one or more *cannabis*-derived drug substances. Preferably, such compositions shall comprise one or more *cannabis*-derived drug products. More preferably, such compositions shall comprise one or more *cannabis*-derived drug products which are substantially free from impurities. Methods of extracting cannabinoids from *Cannabis* plants, and obtaining purified products containing the desired cannabinoids, free from psychoactive compounds such as THC, and free from other impurities, are known in the art and have been described in, e.g., U.S. Pat. Nos. 6,403,126, 8,846,409 and 8,895,078; and U.S. Pat. App. Nos. 2003/0017216A1 and 2016/0038437A1; including references cited.

In preferred embodiments of the invention, the compositions shall comprise one or more synthetic cannabinoids. Preferably, such compositions shall comprise one or more synthetic cannabinoids substantially free from impurities. Synthetic cannabinoids may be generated by means of chemical synthesis from commercially obtainable or otherwise readily available starting materials, using published procedures, such as by way of the methods described in U.S. Pat. Nos. 7,759,526 and 8,071,641, U.S. Pat. App. No. 2010/0298579A1, or by using other methods known to those of ordinary skill in the art.

In other preferred embodiments of the invention, the compositions shall comprise one or more cannabinoids obtained from a bioengineered organism, such as bacteria or yeast. Preferably, such compositions shall comprise one or more bioengineered cannabinoids substantially free from impurities. Bioengineered organisms capable of producing desired cannabinoids can be created, and the cannabinoids can be obtained and purified therefrom, using methods known in the art; see, e.g., U.S. Pat. App. No. 2016/0010126A1.

In some preferred embodiments, the statin is chosen from the group of CYP3A4-metabolized statins, and the cannabinoid is CBD. CBD is also metabolized by CYP3A4 enzymes, as well as acting as a potent inhibitor of CYP3A4. Through both mechanisms CBD is able to displace CYP3A4-metabolized statins and slow their metabolism, resulting in their increased bioavailability, and resulting in pharmaceutical compositions of the invention that can advantageously treat patients with hypercholesterolemia at lower statin dosages and while reducing the risk of adverse effects. Methods of measuring statin and cannabinoid bioavailability have been discussed in, e.g., Huestis, Human Cannabinoid Pharmacokinetics, Chem. Biodivers., 8:1770-1804 (2007); and Garcia et al., Clinical Pharmacokinetics of Statins, Methods Find. Exp. Clin. Pharmacol., 6:457-81 (2003); and references cited.

Similarly, in other preferred embodiments, the statin is chosen from the group of CYP2C19-metabolized statins and CYP2C9-metabolized statins, and the cannabinoid is CBD. CBD is also metabolized by CYP2C19 and CYP2C9 enzymes, as well as acting as a potent inhibitor of those CYP enzymes. Through both mechanisms CBD is able to displace CYP2C19-metabolized statins and CYP2C9-metabolized statins and slow their metabolism, resulting in their increased bioavailability, and resulting in pharmaceutical compositions of the invention that can advantageously treat patients with hypercholesterolemia at lower statin dosages and while reducing the risk of adverse effects.

In more preferred embodiments, the statin is chosen from the group of CYP3A4-metabolized statins, and the cannabinoid is a synthetic cannabinoid having increased affinity for the CYP3A4 enzyme. In yet more preferred embodiments, the cannabinoid is a synthetic cannabidiol having increased affinity for the CYP3A4 enzyme. Although all naturally-occurring cannabidiols, for example, are believed to inhibit the CYP3A4 enzyme, certain synthetic cannabidiols exhibit stronger inhibitory activity when compared against them, and such compounds can be used more advantageously in the pharmaceutical compositions of the invention. Embodiments combining such higher potency cannabinoids with CYP3A4-metabolized statins will exhibit further enhancement of the bioavailability of the statin, as well as of the cannabinoids, as the competitive binding will reduce the metabolism of the cannabinoids by CYP3A4 as well. By using such higher potency cannabinoids, the pharmaceutical compositions of the invention can more advantageously treat patients with hypercholesterolemia at further reduced statin dosages and while also further reducing the risk (in both number and severity) of adverse effects. The evaluation of cannabinoid compounds for their potency as CYP3A4 inhibitors can be performed by using such methods as described in, e.g., Yamaori et al., Potent inhibition of human cytochrome P450 3A isoforms by cannabidiol, Life Sci. 88:730-36 (2011). These and other known methods can be used to compare the potency of CYP3A4 inhibition, for example, of various synthetic cannabidiols to a set of naturally-occurring cannabidiols, or of various other cannabinoid compounds to a set of baseline cannabinoids, to select specific higher potency cannabinoids to be used in the practice of the invention.

Similarly, in other more preferred embodiments, the statin is chosen from the group of CYP2C19-metabolized statins and CYP2C9-metabolized statins, and the cannabinoid is a synthetic cannabinoid having increased affinity for the CYP2C19 and/or CYP2C9 enzymes. In yet more preferred embodiments, the cannabinoid is a synthetic cannabidiol having increased affinity for the CYP2C19 and/or CYP2C9 enzymes. Although all naturally-occurring cannabidiols, for example, are believed to inhibit the CYP2C19 and CYP2C9 enzymes, certain synthetic cannabidiols exhibit stronger inhibitory activity when compared against them, and such compounds can be used more advantageously in the pharmaceutical compositions of the invention. Embodiments combining such higher potency cannabinoids with CYP2C19- and/or CYP2C9-metabolized statins will exhibit further enhancement of the bioavailability of the statin, as well as of the cannabinoids, as the competitive binding will reduce the metabolism of the cannabinoids by those GYP enzymes as well. By using such higher potency cannabinoids, the pharmaceutical compositions of the invention can more advantageously treat patients with hypercholesterolemia at further reduced statin dosages and while also further reducing the risk of adverse effects. The evaluation of cannabinoid compounds for their potency as CYP2C19 inhibitors can be performed by using such methods as described in, e.g., Jiang et al., Cannabidiol is a potent inhibitor of the catalytic activity of cytochrome P450 2C19, Drug Metab. Pharmacokinet., 28(4):332-38 (2013). These and other known methods can be used to compare the potency of CYP2C19 and CYP2C9 inhibition, for example, of various synthetic cannabidiols to a set of naturally-occurring cannabidiols, or of various other cannabinoid compounds to a set of baseline cannabinoids, to select specific higher potency cannabinoids to be used in the practice of the invention.

In other preferred embodiments, the cannabinoid is a cannabinoid selected for its anti-inflammatory activity. In more preferred embodiments, the cannabinoid is a synthetic cannabidiol selected for its anti-inflammatory activity. Although all naturally-occurring cannabidiols, for example, are believed to exhibit some anti-inflammatory activity, certain synthetic cannabidiols exhibit stronger anti-inflammatory activity when compared against them, and such compounds can be used advantageously in the pharmaceutical compositions of the invention. These and other higher potency anti-inflammatory cannabinoids can be chosen to beneficially target both the inflammatory cascades at the root of atherosclerotic lesion development, as well as the inflammatory responses responsible for certain adverse effects of statins therapy (e.g., myositis). By using such higher potency anti-inflammatory cannabinoids, the pharmaceutical compositions of the invention can advantageously treat patients with hypercholesterolemia while reducing the risk of adverse effects. Methods of evaluating cannabinoid compounds for their potency to act as anti-inflammatory agents are described in, e.g., PCT/GB1999/001140, PCT/IL1999/000187, and Calhoun W. et al, Agents and Actions, 21:306-09 (1987). These and other known methods can be used to compare the anti-inflammatory activity, for example, of various synthetic cannabidiols to a set of naturally-occurring cannabidiols, or of various other cannabinoid compounds to a set of baseline cannabinoids, to select specific higher potency anti-inflammatory cannabinoids to be used in the practice of the invention. For example, in Haj et al., HU-444, a Novel, Potent Anti-Inflammatory, Nonpsychotropic Cannabinoid, J. Pharm. (205), the authors report on a synthetic CBD derivative demonstrating increased activity in in vitro and in vivo anti-inflammatory assays. Similarly, in Xu et al., Anti-inflammatory property of the cannabinoid receptor-2-selective agonist JWH-133, J. Leukocyte Bio. 3:532-41 (2007), the authors report on high in vivo anti-inflammatory activity of the synthetic cannabinoid JWH 133.

In still more preferred embodiments, the statin is chosen from the group of CYP3A4-, CYP2C19-, and CYP2C9-metabolized statins, and the cannabinoid is a synthetic cannabidiol that has greater affinity for the same CYP enzyme(s), and also exhibits increased anti-inflammatory activity. In such embodiments, the pharmaceutical compositions of the invention will be understood to be particularly advantageously used to treat patients with hypercholesterolemia while reducing the risk of adverse effects.

In other preferred embodiments, the cannabinoid is a cannabinoid selected for its antioxidant potential. In more preferred embodiments, the cannabinoid is a synthetic cannabidiol selected for its antioxidant potential. Although all naturally-occurring cannabidiols, for example, are believed to exhibit some antioxidant activity, and may therefore limit disease progression in patients with hypercholesterolemia, certain synthetic cannabidiols will exhibit stronger antioxidant potential when compared against them, and such compounds can be used advantageously in the pharmaceutical compositions of the invention. These and other higher potency antioxidant cannabinoids can be chosen to provide additional therapeutic benefits to patients with hypercholesterolemia. By using such higher potency antioxidant cannabinoids, the pharmaceutical compositions of the invention can advantageously treat patients with hypercholesterolemia while reducing the risk of adverse effects. Methods of evaluating cannabinoid compounds for their potency to act as antioxidants are described in, e.g., Cassol et al., Treatment with cannabidiol reverses oxidative stress parameters, Brain Res. 1348:128-38 (2010), and Rajesh et al., Cannabidiol attenuates cardiac dysfunction, oxidative stress, fibrosis, and inflammatory and cell death signaling pathways in diabetic cardiomyopathy, J. Am. Coll. Cardiol., 25:2115-25 (2010). These and other known methods can be used to compare the antioxidant activity, for example, of various synthetic cannabidiols to a set of naturally-occurring cannabidiols, or of various other cannabinoid compounds to a set of baseline cannabinoids, to select specific higher potency antioxidant cannabinoids to be used in the practice of the invention.

In other preferred embodiments, the cannabinoid is a cannabinoid selected for its anti-atherosclerotic potential. In more preferred embodiments, the cannabinoid is a synthetic cannabidiol selected for its anti-atherosclerotic potential. Although all naturally-occurring cannabidiols, for example, are believed to exhibit some anti-atherosclerotic activity, and may therefore reduce the development of atherosclerosis, and limit disease progression in patients with hypercholesterolemia, certain synthetic cannabidiols will exhibit stronger anti-atherosclerotic potential when compared against them, and such compounds can be used advantageously in the pharmaceutical compositions of the invention. These and other higher potency anti-atherosclerotic cannabinoids can be chosen to provide additional therapeutic benefits to patients with hypercholesterolemia. By using such higher potency anti-atherosclerotic cannabinoids, the pharmaceutical compositions of the invention can advantageously treat patients with hypercholesterolemia while reducing the risk of adverse effects. Methods of evaluating cannabinoid compounds for their potency to act as anti-atherosclerotic agents are described in, e.g., Steffens et al., Low dose oral cannabinoid therapy reduces progression of atherosclerosis in mice, Nature 434:782-86 (2005). These and other known methods can be used to compare the anti-atherosclerotic activity, for example, of various synthetic cannabidiols to a set of naturally-occurring cannabidiols, or of various other cannabinoid compounds to a set of baseline cannabinoids, to select specific higher potency anti-atherosclerotic cannabinoids to be used in the practice of the invention.

In still more preferred embodiments, the statin is chosen from the group of CYP3A4-, CYP2C19-, and CYP2C9-metabolized statins, and the cannabinoid is a synthetic cannabidiol that has greater affinity for the same CYP enzyme(s), and also exhibits two or more of: increased anti-inflammatory activity, increased antioxidant activity, and increased anti-atherosclerotic activity. In such embodiments, the pharmaceutical compositions of the invention will be understood to be particularly advantageously used to treat patients with hypercholesterolemia while reducing the risk of adverse effects. In general, it should be understood that selecting for cannabinoids having a combination of beneficial traits would be most advantageous in the practice of the invention, and one would understand how to select for and obtain such cannabinoids, e.g., by using the methods described above in serial (i.e., selecting for the desired traits successively) to evaluate target cannabinoids.

In certain preferred embodiments, it is an object of the invention that the pharmaceutical composition be without psychoactive effect. Methods of measuring the psychoactive effects of cannabinoids will be known to those of ordinary skill, and have been discussed in, e.g., Issa et al., The Subjective Psychoactive Effects of Oral Dronabinol, Clin. J. Pain, 30(6):472-78 (2014). Thus, in some preferred embodiments, the cannabinoid or cannabinoids used shall be substantially free of THC. In such embodiments, it is understood that the pharmaceutical composition of the invention is therefore substantially free of THC. In more preferred embodiments, the composition is entirely free of measurable THC. In some preferred embodiments, the pharmaceutical composition does not produce any psychoactive metabolites. In these and other embodiments, the pharmaceutical composition is without psychoactive effect when taken in a therapeutically active amount. In preferred embodiments, the pharmaceutical composition is without psychoactive effect even at dosages above the therapeutically effective amount. Methods of obtaining purified extracts from *Cannabis* plants containing the desired cannabinoids free from psychoactive compounds such as THC are known in the art and have been described in, e.g., U.S. Pat. No. 6,403,126. One of skill in the art also would understand that the desired cannabinoids for the practice of the invention could be obtained free from THC and other psychoactive cannabinoids by obtaining them through chemical synthesis or from a bioengineered organism.

Excipients, Carriers, and Diluents

According to the present invention, the pharmaceutical composition comprises a pharmaceutically-acceptable excipient. Alternatively, the pharmaceutical composition may comprise a pharmaceutically-acceptable carrier or diluent in addition to or in place of the pharmaceutically-acceptable excipient. Examples of excipients, carriers, and diluents that may be used in these compositions include foods, drinks, lactose, dextrose, sucrose, sorbitol, mannitol, starches, gum, acacia, alginates, tragacanth, gelatin, calcium silicate, microcrystalline cellulose, polyvinylpyrrolidone, polyethylene glycol, cellulose, methyl cellulose, methylhydroxybenzoates, propylhydroxybenzoates, proplhydroxybenzoates, talc, petroleum, and mineral oil. In preferred embodiments, polymeric excipients shall be used; such excipients have been characterized and discussed, for example in Karolewicz, A review of polymers as multifunctional excipients, Saudi Pharm. J., 24:525-36 (2016), and references cited. In other preferred embodiments, excipients which enhance permeability (and hence improve oral bioavailability) shall be used (see Shaikh et al., Permeability Enhancement Techniques for Poorly Permeable Drugs: A review, J. App. Pharma. Sci., 06:34-39 (2012), and references cited). Other excipients, carriers, and diluents that can be used in the practice of the invention shall be known to those of ordinary skill in the art.

It will be understood by those in the art that pharmaceutical excipients useful in the statin-cannabinoid compositions of this invention may further include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumurate and vegetable based fatty acids; and, optionally, a disintegrant, such as croscarmellose sodium, gellan gum, low-substituted hydroxypropyl ether of cellulose, sodium starch glycolate. Other additives useful in the practice of this invention may include plasticizers, pigments, talc, and the like. Such excipients, additives, and other suitable ingredients for use in the practice of the invention are well known in the art (see, e.g., Gennaro, Remington's Pharmaceutical Sciences, 20th Ed.).

It should be apparent that the compositions of the invention are not limited to combinations of a single statin, a single cannabinoid, and a single carrier, diluent, or excipient alone, but also include combinations of multiple statins, multiple cannabinoids, and/or multiple carriers, diluents, and excipients. Pharmaceutical compositions of this invention thus may comprise one or more statins in combination, together with one or more cannabinoids in combination, along with one or more pharmaceutically-acceptable carriers, diluents, and/or excipients.

Further, compositions within the scope of the invention should be understood to be open-ended and may include additional active or inactive compounds and ingredients. For instance, several combination preparations of a statin and another agent exist and would be understood to be able to be used in place of a statin alone in the practice of the present invention. For example, simvastatin/ezetimibe could be used in place of a statin (such as simvastatin alone), in combination with a cannabinoid and a pharmaceutically-acceptable carrier, diluent, or excipient, as could for instance simvastatin/niacin, lovastatin/niacin, or atorvastatin/amlodipine.

Routes of Administration and Dosage

Pharmaceutical dosage unit forms of the present invention are suitable for oral or mucosal (e.g., buccal, sublingual, nasal) administration to a mammal, preferably a human. Suitable dosage forms include, for example, tablets, pills, lozenges, sachets, cachets, elixirs, suspensions, syrups, liquid sprays or drops, soft or hard gelatin capsules, powders, pastes, gels, oral rinses, orally-dissolving films, and the like.

In certain embodiments, it is desired that the pharmaceutical composition be rapidly absorbed into the bloodstream of a mammal through the oral mucosa (i.e., sublingually through the ventral surface of the tongue and floor of the mouth or buccally through tissues lining the cheek and gums). In one such embodiment, the statin-cannabinoid composition comprises an orally-disintegrating dosage form that rapidly disintegrates/disperses in the buccal pouch or sublingual cavity with the help of saliva (i.e., without the need for additional water). Examples of orally-disintegrating dosage forms include fast-melt tablets, chewable tablets, powders, gels, orally-dissolving film strips, and lozenges. In such a form, the time of disintegration should be less than five minutes; or preferably less than four minutes, less than three minutes, less than two minutes, or less than one minute; or more preferably still, less than 30 seconds, less than 20 seconds, or less than 10 seconds.

The pharmaceutical compositions of the invention may be administered and dosed in accordance with good medical practice, taking into account the method and scheduling of administration, prior and concomitant medications and medical supplements, the clinical condition of the individual patient and the severity of the underlying disease, the patient's age, sex, body weight and other such factors relevant to medical practitioners, and knowledge of the particular statin and cannabinoid used. Starting and maintenance dosage levels thus may differ from patient to patient, for individual patients across time, and for different pharmaceutical compositions, but shall be able to be determined with ordinary skill.

The dosage levels of active ingredients comprising the statin-cannabinoid composition may vary depending upon the dosage form and the statin and cannabinoid chosen for administration. The statin-cannabinoid composition generally shall comprise a cannabinoid in an amount effective to lower the effective dose of the selected statin, or to safely allow for higher dosages of the selected statin without the risk (or with a substantially reduced risk) of severe statin-induced adverse effects (e.g., myositis or rhabdomyolysis). For example, when the chosen cannabinoid enhances the bioavailability of the statin (e.g., where the cannabinoid and statin are both substrates of the same CYP enzyme), a lower dose may be used than the commonly-prescribed dosage level for that statin, without loss of therapeutic effect. Additionally, it would be understood that the dose may be successfully lowered a further amount where a larger increase in the bioavailability of the statin is induced; for instance, where the cannabinoid is selected for greater CYP enzyme affinity. Although dosing regimens will vary based on the statin-cannabinoid composition chosen and the characteristics of each individual patient, it shall be understood that the determination of a dosage regimen for a patient will be within the practice of ordinary skill. The following table provides one such example, for a patient switching from a regimen of atorvastatin alone to a composition of atorvastatin and CBD:

| Patient Dosing Example | | |
| --- | --- | --- |
| Atorvastatin alone | Atorvastatin + CBD | Atorvastatin + CBD with greater CYP3A4 Affinity |
| 80 mg | 40 mg + 100 mg | 20 mg + 100 mg |

This example shows that the combination of atorvastatin and CBD allows for a decrease in dosage of the statin of 50%; the combination of atorvastatin and a CBD selected for greater CYP3A4 enzyme affinity allows for a decrease in dosage of the statin of 75%. The advantages of such lower statin doses shall be readily apparent; for instance, the patient who may otherwise have discontinued statin therapy because of intolerance (thus put at increased risk of cardiovascular morbidity and mortality) may now continue statin treatment.

In general, the statin-cannabinoid composition comprises a daily dose of between about 1 mg and about 80 mg of a statin. The statin compounds, when prescribed alone (as with current treatment regimens), are administered at dosages known in the art. See, e.g., 2013 ACC/AHA guideline on the treatment of blood cholesterol to reduce atherosclerotic cardiovascular risk in adults. For example, accepted dosage ranges at the time of this filing include: Fluvastatin sodium is recommended for a 20-80 mg daily oral dose range, preferably between 20 and 40 mg/day for the majority of patients. 20 to 40 mg daily doses are preferably taken once daily at bedtime. 80 mg daily doses is prescribed as 40 mg doses b.i.d. and recommended only for those individuals in whom the 40 mg daily dose is inadequate to lower LDL levels satisfactorily. Atorvastatin has a recommended starting daily dose of 10 mg once daily, with an overall daily dose range of from 10 to 80 mg. Simvastatin may be administered with a starting dose of 20 mg once a day in the evening, or a 10 mg dose per day for those requiring only a moderate reduction in LDL levels. The recommended overall daily dosage range taken as a single evening dose is from 5 to 80 mg. Pravastatin sodium has a recommended starting dose of 10 or 20 mg per day, taken daily as a single dose at bedtime, with a final overall daily range of from 10 to 40 mg. Lovastatin has a recommended daily starting dosage of 20 mg per day taken with the evening meal. The recommended final daily dosage range is from 10 to 80 mg per day in single or di doses. Pitavastatin, the most recently approved drug in this class, is administered in a dose range of between 1-4 mg per day. In general, these statins are formulated in a simple oral dosage unit form. The accepted and commonly-prescribed dosage ranges for individual statins may vary over time due to new medical evidence, which may be incorporated into new guidelines, but standard dosage ranges shall be known or readily available to those of ordinary skill in the art. The standard dosage range for each statin is thus understood to have a lowest and highest recommended dose when administered alone (which may differ for dosage type and regimen, but would nevertheless be known for each set of parameters by those of ordinary skill).

Consistent with the aim of the present invention to reduce statin-induced side effects, and to reduce statin dosages without loss of therapeutic effect, it is generally preferred that the statin dose be less than or equal to 40 mg/day. For example, in one such embodiment, the statin dose will be less than or equal to 25 mg/day. In another embodiment, the statin dose will be less than or equal to 20 mg/day. In yet another embodiment, the statin dose will be less than or equal to 10 mg/day. In yet another embodiment, the statin dose will be less than or equal to 5 mg/day. In yet another embodiment, the statin dose will be less than or equal to 2 mg/day. In yet another embodiment, and by way of further example, the statin dose will be less than or equal to 1 mg/day. The statin dose selected for each individual subject shall be able to be determined by one of ordinary skill, based on the subject's background and needs, in view of good medical practice, and in light of the aims of the present invention to reduce statin-induced side effects and to reduce statin dosages without loss of therapeutic effect. One of ordinary skill would further understand how to determine whether a reduced dosage is as therapeutically effective as a patient's prior dosage, based on the patient's medical history and current treatment. Additionally, one of ordinary skill would understand how to determine whether the adverse effects of statin treatment are reduced for a patient, based on clinically accepted criteria. (See, e.g., Rosenson (2017); Hovingh et al., Identification and management of patients with statin-associated symptoms in clinical practice, 245: 111-17 (2016); and references cited.)

In certain embodiments, the statin-cannabinoid composition comprises a daily dose of between about 1 mg and about 500 mg of a cannabinoid. To provide for a single-dosage form of the statin-cannabinoid composition, it is generally preferred that the cannabinoid dose be less than or equal to 100 mg/day. For example, in one such embodiment, the cannabinoid dose will be less than or equal to 50 mg/day. In another embodiment, the cannabinoid dose will be less than or equal to 25 mg/day. In another embodiment, the cannabinoid dose will be less than or equal to 20 mg/day. In another embodiment, the cannabinoid dose will be less than or equal to 10 mg/day. In another embodiment, the cannabinoid dose will be less than or equal to 5 mg/day. In another embodiment, the cannabinoid dose will be less than or equal to 2 mg/day. In yet another embodiment, and by way of further example, the cannabinoid dose will be less than or equal to 1 mg/day. The cannabinoid dose selected for each individual subject shall be able to be determined by one of ordinary skill, based on the subject's background and needs, in view of good medical practice, and in light of the aims of the present invention to reduce statin-induced side effects and to reduce statin dosages without loss of therapeutic effect.

In certain preferred embodiments, the statin-cannabinoid composition comprises a daily dose of between about 1 mg and about 500 mg of a CBD. To provide for a single-dosage form of the statin-CBD composition, it is generally preferred that the cannabidiol dose be less than or equal to 100 mg/day. For example, in one such embodiment, the CBD dose will be less than or equal to 50 mg/day. In another embodiment, the CBD dose will be less than or equal to 25 mg/day. In another embodiment, the CBD dose will be less than or equal to 20 mg/day. In another embodiment, the CBD dose will be less than or equal to 10 mg/day. In another embodiment, the CBD dose will be less than or equal to 5 mg/day. In another embodiment, the CBD dose will be less than or equal to 2 mg/day. In yet another embodiment, and by way of further example, the CBD dose will be less than or equal to 1 mg/day. The CBD dose selected for each individual subject shall be able to be determined by one of ordinary skill, based on the subject's background and needs, in view of good medical practice, and in light of the aims of the present invention to reduce statin-induced side effects and to reduce statin dosages without loss of therapeutic effect. In determining dosages, one also would understand that the effective dose of CBD may be determined in part in view of the biphasic dose curve for CBD (i.e., a U-shaped dose-response curve in which efficacy is optimal between low and high doses).

Optionally, the daily dose of statin-cannabinoid composition may be administered as a single dose (i.e., one time per day), or divided into multiple doses (e.g., two, three, or more doses) over the course of a day.

In another embodiment the pharmaceutical composition of the present invention may be prepared, packaged or sold in a titratable dosage form. The term "titrate" is defined as meaning that the patient is provided with a medication that is in such a form that smaller doses than the unit dose can be taken. A "unit dose" is defined as a maximum dose of medication that can be taken at any one time or within a specified dosage period. Titration of doses is beneficial to the patient as they are able to increase the dose incrementally until the drug is efficacious. It is understandable that not all patients will require exactly the same dose of medication, for example patients of a relatively larger build or faster metabolism may require a higher dose. Different patients may also present with different degrees of complaints and as such may require larger or smaller doses in order to treat the complaint effectively. The benefits of a titratable dosage form over a standard dosage form, which would have to be split into a partial dose, are therefore evident.

In some embodiments, the pharmaceutical composition of the present invention may be prepared, packaged or sold in a formulation suitable for oral digestive administration. Such formulations may, for example, be in solid dosage form such as pills, tablets, capsules, or may be in liquid form. In some preferred embodiments, the pharmaceutical composition comprises an effervescent dosage form such as an effervescent tablet. In other preferred embodiments, the composition is a multi-layer tablet. Methods of preparing formulations suitable for oral administration include, for example, those described in WO2005/034908A2, and references cited.

In other embodiments, the pharmaceutical composition of the present invention may be prepared, packaged or sold in a formulation suitable for buccal administration. Such formulations may, for example, be in the form of buccal tablets, bioadhesive particles, wafers, lozenges, medicated chewing gums, adhesive gels, patches, films, a paste, an ointment, or an aerosol.

In yet other embodiments, the pharmaceutical composition of the present invention may be prepared, packaged or sold in a formulation suitable for sublingual administration. Such formulations may, for example, be in the form of sublingual tablets, drops, films, sprays or aerosols, or lozenges.

Preparation of statin formulations suitable for buccal or sublingual administration has been described in, e.g., U.S. Pat. App. Nos. 2015/0328142A1, US2003/0162827A1, and PCT/US2002/021287.

Notably, buccal or sublingual administration allows for near-instantaneous adsorption of the statin into the blood stream through the oral mucosa in contrast to conventional oral administration, which typically takes from one to two hours after administration by the oral digestive route. Moreover, the buccal and sublingual formulations of the present invention allow for even lower dosages of statin to be given without loss of therapeutic effect, because delivery (of both the statin and the cannabinoid) bypasses GI and first pass metabolism.

Administration of the pharmaceutical compositions of the invention, such as the embodiments described above, are therefore advantageously used to treat hypercholesterolemia and atherosclerosis in a subject, as well as to treat or prevent myositis, rhabdomyolysis or statin-associated myopathy in a subject.

The invention claimed is:

1. A pharmaceutical composition in unit dosage form for once daily dosing, useful in treating a patient with a lipid disorder, which consists essentially of a statin-cannabidiol combination of:
    (a) a reduced daily dosage amount of a statin; and
    (b) less than or equal to 500 mg of a cannabidiol;
    together with a pharmaceutically acceptable carrier, diluent, or excipient; wherein the reduced daily dosage amount of the statin is less than the lowest standard daily dosage amount for the statin when taken alone; and wherein the pharmaceutical composition is formulated for oral or mucosal administration and the statin-cannabidiol combination confers a synergistic effect compared to the statin and the cannabidiol administered alone in the same amounts, said synergistic effect responsible for the reduced daily dosage amount of the statin without loss of therapeutic effect, and wherein the statin is atorvastatin.

2. The pharmaceutical composition of claim 1, wherein the atorvastatin is present in the unit dosage form in an amount of between 5-10 mg.

3. The pharmaceutical composition of claim 1, wherein the atorvastatin is present in the unit dosage form in an amount of between 2-5 mg.

4. The pharmaceutical composition of claim 1, wherein the statin is present in the unit dosage form in an amount of between 1-2 mg.

5. The pharmaceutical composition of claim 1, wherein the atorvastatin is present in the unit dosage form in an amount of less than 1 mg.

6. The pharmaceutical composition of claim 1, wherein the unit dosage form is suitable for oral administration, and atorvastatin and the cannabidiol both undergo first-pass metabolism after administration.

7. The pharmaceutical composition of claim 1, wherein the unit dosage form is suitable for buccal or sublingual administration.

8. A pharmaceutical composition for once daily dosing, useful in treating a patient with a lipid disorder, which consists essentially of a statin-cannabidiol combination of therapeutically effective amounts of:
    (a) a reduced daily dosage amount of a statin; and
    (b) a cannabidiol;
    wherein the reduced daily dosage amount of the statin is less than the lowest standard daily dosage amount for the statin when taken alone; and wherein the pharmaceutical composition is formulated for oral or mucosal administration and the statin-cannabidiol combination confers a synergistic effect compared to the statin and the cannabidiol administered alone in the same amounts, said synergistic effect responsible for the reduced daily dosage amount of the statin without loss of therapeutic effect, and wherein the statin is atorvastatin.

9. The pharmaceutical composition of claim 8, wherein the reduced daily dosage amount of the atorvastatin is no greater than 50% of the lowest standard daily dosage amount for the atorvastatin when taken alone.

10. The pharmaceutical composition of claim 8, wherein the reduced daily dosage amount of atorvastatin is no greater than 25% of the lowest standard daily dosage amount for atorvastatin when taken alone.

11. The pharmaceutical composition of claim 8, wherein the atorvastatin and the cannabidiol are both substrates of the same CYP enzyme, and the atorvastatin and the cannabidiol both undergo first-pass metabolism after administration by said CYP enzyme.

12. The pharmaceutical composition of claim 8, wherein the cannabidiol has been selected for greater affinity for a CYP enzyme.

13. A method of treating a medical condition in a human in need of such treatment, the method comprising administering in combination to the human a synergistically and therapeutically effective amount of atorvastatin and a cannabidiol, and wherein the medical condition is selected from the group consisting of a dysregulation of cholesterol metabolism, myositis, rhabdomyolysis, and statin-associated myopathy.

14. The method of claim 13 wherein the medical condition is hypercholesterolemia.

15. The method of claim 13 wherein the medical condition is atherosclerosis.

\* \* \* \* \*